United States Patent [19]

Brugge et al.

[11] Patent Number: 4,827,026

[45] Date of Patent: May 2, 1989

[54] METHOD FOR PRODUCING 5-T-BUTYLISOPHTHALIC ACID

[75] Inventors: Stephen P. Brugge; Jon J. Harper; Larry W. Autry, all of Naperville, Ill.

[73] Assignee: Amoco Corporation, Chicago, Ill.

[21] Appl. No.: 124,978

[22] Filed: Nov. 24, 1987

[51] Int. Cl.$^4$ .................. C07C 51/215; C07C 51/43; C07C 51/487
[52] U.S. Cl. .................................. 562/416; 562/417; 562/486; 562/487
[58] Field of Search ................ 562/416, 417, 486, 487

[56] References Cited

U.S. PATENT DOCUMENTS 3,344,177   9/1967   Hensley et al. .................... 562/485

Primary Examiner—Werren B. Lone
Assistant Examiner—Vera C. Clarke
Attorney, Agent, or Firm—James R. Henes; William H. Magidson; Ralph C. Medhurst

[57] ABSTRACT

A method is disclosed for producing purified 5-t-butylisophthalic acid by the liquid-phase oxidation of 5-t-butyl-m-xylene in a solvent and in the presence of a catalyst comprising cobalt, manganese and bromine components.

7 Claims, No Drawings

METHOD FOR PRODUCING 5-T-BUTYLISOPHTHALIC ACID

BACKGROUND OF THE INVENTION

1. Field of the Invention

This invention relates generally to a method for producing relatively pure 5-t-butylisophthalic acid by the liquid-phase oxidation of 5-t-butyl-m-xylene in a solvent.

2. Discussion of the Prior Art

Over approximately the past three decades, organic compounds in which two or more carboxylic acid groups are bonded to one or more aromatic nuclei have become of increasing interest, either as direct components in or as intermediates for synthetic condensation polymer molecules. More particularly, one such aromatic polycarboxylic acid, 5-t-butylisophthalic acid, has been employed in the preparation of many polymers, such as polyesters, polyarylates, polyamides and polyarylamides.

Obviously, the presence of impurities in 5-t-butylisophthalic acid can have a serious adverse effect on the physical or chemical properties or performance characteristics of any formulation containing 5-t-butylisophthalic acid itself or any polymer formed from 5-t-butylisophthalic acid. In addition, impurities in 5-t-butylisophthalic acid can adversely affect polymerization processes to which the 5-t-butylisophthalic acid is subjected. Such impurities in 5-t-butylisophthalic acid formed by the liquid-phase oxidation of 5-t-butyl-m-xylene in the presence of a catalyst comprising cobalt, manganese and bromine are often organic impurities or by-products formed during the oxidation and inorganic impurities corresponding to metal components of the catalysts employed in the oxidation or formed therefrom. Such impurities often impart undesirable color characteristics to the 5-t-butylisophthalic acid and its polymerization products.

The major impurity formed in the liquid-phase oxidation of 5-t-butyl-m-xylene to form 5-t-butylisophthalic acid in a $C_2$–$C_6$ monocarboxylic acid solvent and in the presence of an oxidation catalyst comprising cobalt, manganese, and bromine components is trimesic acid, which is formed by the oxidation of the t-butyl group in 5-t-butyl-m-xylene. Trimesic acid is a trifunctional acid and will cause branching in polymers, which at high levels leads to brittleness. In addition, the formation of trimesic acid represents a reduction in the yield of 5-t-butylisophthalic acid.

Thus, maximization of the yield of 5-t-butylisophthalic acid and minimization of the formation of undesirable by-products, especially trimesic acid, during the oxidation of 5-t-butyl-m-xylene, and the removal of such by-products from the resulting crude 5-t-butylisophthalic acid product are highly desirable. One of the difficulties with the prior art procedures for the aforesaid oxidation and purification lies in their inability to provide an essentially pure product without expensive and time-consuming separation procedures. Generally, where polyalkyl derivatives are employed as reactants, the reaction sometimes appears to proceed with the oxidation of one of the alkyl radicals to the exclusion of the remainder. Such by-products frequently tend to possess solubility properties similar to those possessed by the desired product, making separation and purification of the desired product expensive and time-consuming in commercial operations. A further difficulty encountered in such reactions involving the formation of intermediate oxidation products resides in the fact that conditions and catalyst materials which function most efficiently at one stage of the reaction may become less efficient for oxidation at another intermediate stage.

Furthermore, the removal of organic and inorganic impurities from aromatic polycarboxylic acids, including 5-t-butylisophthalic acid, formed by the catalyzed, liquid-phase oxidation of polyalkyl aromatics is typically very difficult, and the removal technique employed depends on the specific aromatic polycarboxylic acid from which the impurities are to be removed and the specific oxidation conditions and catalyst employed to make it. Furthermore, techniques for purifying aromatic polycarboxylic acids are often relatively time-consuming and involve relatively complex reaction schemes.

For example, Hensley et al., U.S. Pat. No. 3,344,177 illustrates the complexity of prior art purification methods. This patent discloses in Example 11 a method for purifying crude t-butylisophthalic acid that was prepared by the liquid-phase oxidation of t-butyl-m-xylene in acetic acid with air and in the presence of a bromine-promoted heavy metal oxidation catalyst, and then by washing the solid t-butylisophthalic acid with acetic acid and drying the washed t-butylisophthalic acid. Hensley et al. does not disclose the atomic ratio of bromine-to-heavy metal catalyst component or the temperature employed for the oxidation. The crude t-butylisophthalic acid is dissolved with aqueous sodium hydroxide. The resulting solution is filtered and acidified to a pH of about 6.0. A portion of the solution containing 3 pounds of dissolved crude acid is percolated at ambient temperature through 2.5 pounds of PCC CAL activated carbon in a column two inches in diameter and four feet long. The percolation effluent is filtered to remove carbon fines (no pretreatment of carbon bed with water), diluted 1 to 1 with water, and admixed with a 20% sulfuric acid solution heated to 194° F. to a pH of about 2 to 3 to regenerate solid t-butylisophthalic acid. The precipitated t-butylisophthalic acid is recovered by filtration; the filter cake is washed with distilled water, slurried in boiling distilled water, and recovered again by filtration and dried at 140° F.

Therefore, it is highly desirable to produce 5-t-butylisophthalic acid under conditions such that the production of impurities and their incorporation in the crude 5-t-butylisophthalic acid product are minimized and the yield of such higher quality 5-t-butylisophthalic acid is improved and to purify the crude 5-t-butylisophthalic acid by a relatively simpler and shorter procedure to obtain 5-t-butylisophthalic acid having the requisite purity.

OBJECTS OF THE INVENTION

It is therefore a general oject of the present invention to provide an improved method for producing 5-t-butylisophthalic acid which overcomes the aforesaid problems of the prior art methods.

More particularly, it is an object of the present invention to provide an improved method for oxidizing 5-t-butyl-m-xylene in the liquid-phase in a $C_2$–$C_6$ monocarboxylic acid solvent and in the presence of an oxidation catalyst comprising cobalt, manganese and bromine components, to form crude 5-t-butylisophthalic acid of substantially improved purity.

It is a related object of the present invention to provide an improved method for purifying the crude 5-t-butylisophthalic acid formed by the liquid-phase oxidation of 5-t-butyl-m-xylene in a $C_2$–$C_6$ monocarboxylic acid solvent in the presence of an oxidation catalyst comprising cobalt, manganese and bromine components.

Other objects and advantages of the present invention will become apparent upon reading the following detailed description and appended claims.

SUMMARY OF THE INVENTION

These objects are achieved by an improved method for producing 5-t-butylisophthalic acid comprising oxidizing 5-t-butyl-m-xylene with an oxygen-containing gas in the liquid phase in a solvent comprising an aliphatic monocarboxylic acid having 2 to 6 carbon atoms at an elevated pressure, at a temperature in the range of from about 150° C. to about 230° C. and in the presence of an oxidation catalyst comprising cobalt, manganese, and bromine components, to form a product mixture comprising crude 5-t-butylisophthalic acid, wherein the atom ratio of cobalt (calculated as elemental cobalt) in the cobalt component of the catalyst-to-5-t-butyl-m-xylene in the liquid-phase oxidation is in the range of from about 0.1 to about 20 milligram atoms (mga) per gram mole of 5-t-butyl-m-xylene, the atom ratio of manganese (calculated as elemental manganese) in the manganese component of the catalyst-to-cobalt (calculated as elemental cobalt) in the cobalt component of the catalyst is in the range of from about 0.5 to about 3 mga per mga of cobalt, and the atom ratio of bromine (calculated as elemental bromine) in the bromine component of the catalyst-to-total cobalt and manganese (calculated as elemental cobalt and elemental manganese) in the cobalt and manganese components of the catalyst is in the range of from about 0.2 to about 0.5 mga per mga of total cobalt and manganese, and wherein the reaction temperature is in the range of from about 150° C. to about 230° C.

DETAILED DESCRIPTION OF THE PREFERRED EMBODIMENTS

Suitable solvents for use in the oxidation step of the method of the present invention for producing 5-t-butylisophthalic acid include any aliphatic $C_2$–$C_6$ monocarboxylic acid such as acetic acid, propionic acid, n-butyric acid, isobutyric acid, n-valeric acid, trimethylacetic acid, and caproic acid, and mixtures thereof with water. Preferably, the solvent is a mixture of acetic acid and water, which more preferably contains from 1 to 20 weight percent of water and most preferably from 2 to 10 weight percent of water, as introduced into the oxidation reactor (rather than formed in the reactor during the reaction) and based on the weight of the total solvent. Since heat generated in the highly exothermic liquid-phase oxidation is dissipated at least partially by vaporization of solvent in the oxidation reactor, some of the solvent is withdrawn from the reactor as a vapor, which is then condensed and recycled to the reactor. In addition, some solvent is withdrawn from the reactor as a liquid in the product stream. After separation of the crude 5-t-butylisophthalic acid product from the product stream, at least a portion of the mother liquor (solvent) in the resulting product stream is recycled to the reactor. The weight ratio of the total amount of the monocarboxylic acid solvent-to-total amount of 5-t-butyl-m-xylene added during the entire oxidation step in the method of this invention is 2:1 to 7:1.

The source of molecular oxygen employed in the oxidation step of the method of this invention can vary in molecular oxygen content from that of air to oxygen gas. Air is the preferred source of molecular oxygen. In order to avoid the formation of explosive mixtures, the oxygen-containing gas fed to the reactor should provide an exhaust gas-vapor mixture containing from 0.5 to 8 volume percent oxygen and preferably from 2 to 6 volume percent oxygen (measured on a solvent-free basis). For example, a feed rate of the oxygen-containing gas sufficient to provide oxygen in the amount of from 1.5 to 2.8 moles per oxidizable methyl group of the 5-t-butyl-m-xylene will provide such 0.5 to 8 volume percent of oxygen (measured on a solvent-free basis) in the gas-vapor mixture in the condenser.

The catalyst employed in the oxidation step of the method for producing purified 5-t-butylisophthalic acid for use in combination with the method of this invention comprises cobalt, manganese, and bromine components, and can additionally comprise accelators known in the art. The atom ratio of cobalt (calculated as elemental cobalt) in the cobalt component of the catalyst-to-5-t-butyl-m-xylene in the liquid-phase oxidation is in the range of from about 0.1 to about 20 milligram atoms (mga) per gram mole of 5-t-butyl-m-xylene. The atom ratio of manganese (calculated as elemental manganese) in the manganese component of the catalyst-to-cobalt (calculated as elemental cobalt) in the cobalt component of the catalyst in the liquid-phase oxidation is in the range of from about 0.5 to about 3 mga per mga of cobalt. The atomic ratio of bromine (calculated as elemental bromine) in the bromine component of the catalyst-to-total cobalt and manganese (calculated as elemental cobalt and elemental manganese) in the cobalt and manganese components of the catalyst in the liquid-phase oxidation is in the range of from about 0.2 to about 0.5 mga per mga of total cobalt and manganese.

Each of the cobalt and manganese components can be provided in any of its known ionic or combined forms that provide soluble forms of cobalt, manganese, and bromine in the solvent in the reactor. For example, when the solvent is an acetic acid medium, cobalt and-/or manganese carbonate, acetate tetrahydrate, and/or bromine can be employed. The 0.2:1 to 0.5:1 bromine-to-total cobalt and manganese milligram atom ratio is provided by a suitable source of bromine. Such bromine sources include elemental bromine ($Br_2$), or ionic bromide (for example, HBr, NaBr, KBr, $NH_4Br$, etc.), or organic bromides which are known to provide bromide ions at the operating temperature of the oxidation (e.g., bromobenzenes, benzylbromide, mono- and dibromoacetic acid, bromoacetyl bromide, tetrabromoethane, ethylene-di-bromide, etc.). The total bromine in molecular bromine and ionic bromide is used to determine satisfaction of the elemental bromine-to-total cobalt and manganese milligram atom ratio of 0.2:1 to 0.5:1. The bromine ion released from the organic bromides at the oxidation operating conditions can be readily determined by known analytical means. Tetrabromoethane, for example, at operating temperatures of 170° to 225° C. has been found to yield about 3 effective gram atoms of bromine per gram mole.

In operation, the minimum pressure at which the oxidation reactor is maintained is that pressure which will maintain a substantial liquid phase of the 5-t-butyl-m-xylene and at least 70 percent of the solvent. The 5-t-butyl-m-xylene and solvent not in the liquid phase because of vaporization are removed from the oxidation reactor as a vapor-gas mixture, condensed, and then returned to the oxidation reactor. When the solvent is an acetic acid-water mixture, suitable reaction gauge pressures in the oxidation reactor are in the range of from about 2.5 kg/cm$^2$ to about 35 kg/cm$^2$, and typically are in the range of from about 10 kg/cm$^2$ to about 30 kg/cm$^2$. The temperature range within the oxidation reactor is generally from about 150° C., preferably from about 175° C., to about 230° C., preferably to 205° C. The solvent residence time in the oxidation reactor is generally from about 20 to about 150 minutes and preferably from about 30 to about 120 minutes.

The oxidation of the method of this invention can be performed either on a batch, continuous or semi-continuous mode. In the batch mode, the 5-t-butyl-m-xylene solvent and the cobalt, manganese and bromine components are initially introduced batchwise into the reactor, and the temperature and pressure of the reactor contents are then raised to the desired levels therefor for the commencement of the oxidation reaction. Air is introduced continuously into the reactor. After commencement of the oxidation reaction—for example, after all of the 5-t-butyl-m-xylene had been completely introduced into the reactor, the temperature of the reactor contents is raised. In the continuous mode, each of the 5-t-butyl-m-xylene, air, solvent and the catalyst components dissolved in the solvent are continuously introduced through a first inlet or set of inlets into a first oxidation reactor where the temperature and pressure are at the desired levels therefor for initiation of the oxidation reaction; and a product stream comprising the 5-t-butylisophthalic acid product and catalyst components dissolved in the solvent is withdrawn from the reactor. In the semi-continuous mode, the solvent and the cobalt, manganese, and bromine components are initially introduced batchwise into the reactor, and then the 5-t-butyl-m-xylene reactant and air are introduced continuously into the reactor. After commencement of the oxidation reaction, the temperature of the reactor contents is raised. Preferably, the semi-continuous mode is employed for the oxidation of the method of this invention, with the temperature of the reactor contents at about 150°–205° C. when 5-t-butyl-m-xylene is first introduced and rising to a steady-state temperature of about 170°–230° C. as the exothermic oxidation proceeds and with the 5-t-butyl-m-xylene being introduced at 0.05–1.0 parts per part of solvent by weight per hour for 0.3–3.0 hours. Preferably the reaction temperature is 175° C.–205° C.

In each case, the progress of the reaction is monitored by measuring oxygen uptake and temperature changes. A run is terminated after oxygen uptake ceases, as evidenced by a rapid decrease in oxygen uptake—that is, by a rapid increase in the oxygen concentration in the vapor-gas mixture withdrawn from the reactor.

Thereafter, the product stream in the continuous mode or the reactor contents in the batch or semi-continuous mode are cooled at a rate of about 25°–140° C. per hour to a temperature in the range of from about 20° C. to about 120° C. in at least one step and in at least one crystallizer such that essentially all of the resulting crude, solid 5-t-butylisophthalic acid product is separated from the product mixture typically by filtration or centrifugation at a temperature in the range of from about 20° C. to about 120° C. The use of lower temperatures results in the recovery of a significantly less pure product and the use of higher temperatures results in the recovery of significantly less product.

The purification step of the method of this invention involves recrystallization of the crude 5-t-butylisophthalic acid from a recrystallization solvent which comprises 0–100 weight percent of water and 0–100 weight percent of acetic acid, containing at least 80 weight percent of acetic acid. Preferably the recrystallization solvent is a mixture of water and acetic acid. More preferably, the recrystallization solvent is a mixture of water and acetic acid, containing at least 80 weight percent of acetic acid, based on the total weight of the recrystallization solvent. One part of the crude 5-t-butylisophthalic acid and from about 2 to about 7 parts by weight of recrystallization solvent are combined at a temperature of from about 160° C. to about 260° C. The resulting solution is then cooled to a temperature of from about 20° C. to about 120° C. at a rate of from about 28° C. to about 140° C. per hour with a crystallization time of from about 1 to about 5 hours.

Optionally the dissolved crude 5-t-butylisophthalic acid is hydrogenated by means of a hydrogen gas stream in the presence of a hydrogenation catalyst such as a nobel metal. Preferably a nobel metal deposited on a support such as a carbon support—for example, palladium-on-carbon catalyst particles—are employed as the hydrogenation catalyst. Preferably, such hydrogenation is included in the purification step when the recrystallization solvent does not contain acetic acid.

The purification step of the method of this invention further substantially reduces the content of trimesic acid in the 5-t-butylisophthalic acid and in addition substantially reduces the contents of 5-t-butyl-3-carboxybenzaldehyde and 5-t-butyl-m-toluic acid, the two other major organic impurities formed in the oxidation step of the method of this invention and of the cobalt, manganese and bromine impurities which result from the catalyst components employed in the oxidation step.

The present invention will be more clearly understood from the following specific examples:

EXAMPLES 1–12

Each of Examples 1–12 involves the oxidation of 5-t-butyl-m-xylene on a semi-continuous basis. The reactor employed was a one-liter reactor equipped with a stirrer, air line, cooling coil, and a line for introduction of air during the oxidation. The temperature of the reactor was controlled by insulated electrical heaters which surrounded the autoclave, and the cooling coil in the reactor. A controlled rate of fluid was passed through the cooling coil during the oxidation. The vented gases from the reactor were passed through a series of condensers, cooled by dry-ice, and then through instruments which recorded the gaseous flow rate and the concentration of oxygen and carbon oxides in the gas stream. In these examples, an acetic acid solvent (including water added from an external source—that is, in the total of new and recycled solvent—at a concentration of 5 weight percent based on the acetic acid) and the cobalt, manganese (added in the form of their acetate tetrahydrates), and bromine (added as HBr) components of the catalyst were introduced batchwise into the reactor. The reactor was purged and then pressurized to 300 pounds per square inch gauge with a slow addition of nitrogen gas. The temperature of the reactor contents was raised to the desired level therefor for commencement of the oxidation, and then 5-t-butyl-m-xylene at a rate of 2 milliliters per minute and air were introduced continuously into the reactor. Immediately after all of the 5-t-butyl-m-xylene had been introduced (which required 72 minutes in each of Examples 1-12), the temperature of the reactor contents was raised to the reaction temperature. The pressure of the reactor was controlled by a research control valve. The rate of oxidation was determined by measuring the oxygen content of the vent gas and knowing the flow rate of air through the reactor, and was employed as a measure of the extent of conversion of the reactant. The reaction was terminated after oxygen uptake had ceased and the oxygen content of the vent gas exceeded 12 mole percent, whereupon the flow of air into the reactor was replaced by a flow of nitrogen gas into the reactor. In each of Examples 1-12, the final or total weight ratio of acetic acid solvent-to-5-t-butyl-m-xylene added to the reactor over the entire length of the run was 4:1. Additional experimental conditions employed in and the results from Examples 1-12 are presented in Table 1.

TABLE 1

| Example No. | Catalyst Composition | | | React. Temp.[3] | Carbon Oxide Yield[4] | Trimesic Acid Content[5] |
|---|---|---|---|---|---|---|
| | Co[1] | Co:Mn:Br[2] | (Co + Mn):Br[2] | | | |
| 1 | 0.026 | 1:2:1.02 | 1:0.34 | 195.5 | 0.6 | 0.36 |
| 2 | 0.026 | 1:2:1.02 | 1:0.34 | 196 | 0.9 | 1.26 |
| 3 | 0.026 | 1:2:1.00 | 1:0.33 | 195 | 0.6 | 1.03 |
| 4 | 0.026 | 1:2:1.08 | 1:0.36 | 196 | 0.7 | 0.68 |
| 5 | 0.026 | 1:1:0.46 | 1:0.23 | 195.5 | 0.6 | 0.59 |
| 6 | 0.026 | 1:3:0.80 | 1:0.20 | 196 | 0.6 | 0.70 |
| 7 | 0.013 | 1:3:0.84 | 1:0.21 | 207 | 0.6 | 0.79 |
| 8 | 0.052 | 1:1:0.40 | 1:0.20 | 207 | 1.2 | 1.19 |
| 9 | 0.013 | 1:3:4.00 | 1:1.0 | 197 | 0.9 | 3.35 |
| 10 | 0.052 | 1:1:2.00 | 1:1.00 | 196 | 1.3 | 4.57 |
| 11 | 0.026 | 1:1:2.00 | 1:1.00 | 207 | 1.8 | 4.51 |
| 12 | 0.026 | 1:3:4.04 | 1:1.01 | 207 | 1.9 | 6.64 |

[1]Weight percent of acid solvent
[2]Atomic ratio
[3]°C.
[4]Moles per mole of 5-t-butyl-m-xylene
[5]As weight percent of crude 5-t-butylisophthalic acid Comparison of the results in Table 1 for Examples 1-6 illustrates that neither the total weight percent of catalyst metals employed nor the atomic ratio of the cobalt-to-manganese catalyst components has a substantial effect on either the yield of carbon monoxide or the content of trimesic acid in the crude 5-t-butylsophthalic acid product.

Comparison of the results in Table 1 for Examples 1-6 with the results for Examples 9-12 illustrates that, when an atomic ratio of total cobalt and manganese-to-bromine of 1:1 is employed both the content of trimesic acid in the crude 5-t-butylisophthalic acid and the yield of carbon oxides increase.

Comparison of the results in Table 1 for Examples 5-8 illustrates that, when the reaction temperature is 207° C., even when the atomic ratio of total cobalt and manganese-to-bromine is 1:0.2, there is an increased dependence of both the yield of carbon oxides and the content of trimesic acid in crude 5-t-butylisophthalic acid on the atomic ratio of the cobalt-to-manganese catalyst components.

EXAMPLES 13-16

Each of Examples 13-16 was performed using a reactor equipped with a stirrer and means for controlling the temperature. In each case, crude 5-t-butylisophthalic prepared in accordance with the method of this invention, acid was dissolved in the recrystallization solvent by heating their admixture to a solution temperature. In Examples 13-15, a one-gallon reactor was used, and each solution was cooled to 95° C. by cooling at a rate of 100° C. per hour. In Example 14 only, the recrystallization solution was contacted with 4.3 grams of palladium-on-carbon hydrogenation catalyst and hydrogen was passed through this mixture. In Example 16, a 100 gallon reactor was used, and the solution was cooled to 71° C. at about 60° C. per hour.

The remaining conditions employed in and the results from Examples 13-16 are presented in Table 2.

TABLE 2

| Example No. | 13 | 14 | 15 | 16 |
|---|---|---|---|---|
| Conditions | | | | |
| Amounts[1] | | | | |
| Crude 5-t-butyl-isophthalic acid | 245 | 325 | 600 | 60[2] |
| Recrystallization solvent | 980 | 1300 | 2400 | 240[2] |
| Recrystallization Solvent Composition[3] | | | | |
| Water | 100 | 100 | 50 | 15 |
| Acetic Acid | | | 50 | 85 |
| Solution Temperature (C.°) | 246 | 246 | 204 | 204 |
| Results | | | | |
| Yield[4] of 5-t-butylisophthalic | 94 | 94 | 92 | 87 |
| Percent reduction[5] | | | | |
| Trimesic acid | >90 | >90 | >90 | >90 |
| 5-t-butyl-3-carboxybenzaldehyde | 40 | 60 | 40 | 90 |
| 5-t-butyl-m-toluic acid | 20 | 30 | 80 | 90 |
| Bromine | 70 | 75 | 75 | 75 |
| Cobalt | >90 | >90 | >90 | >85 |
| Manganese | >90 | >90 | >90 | >90 |
| Optical density | 15 | 85 | 70 | 80 |

[1]Grams
[2]Pounds
[3]Weight percent of total solvent
[4]Based on the weight of crude 5-t-butylisophthalic acid
[5]Based on the level of the impurity or parameter in crude 5-t-butylisophthalic acid The results in Table 2 illustrate that the lowest levels of impurities and of optical density are achieved when the recrystallization solvent is a mixture of acetic acid and water containing less than 20 weight percent of water. When water is the recrystallization solvent, the lowest levels of impurities and optical density are achieved when the solution is contacted with hydrogen and a hydrogenation catalyst.

From the above description, it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

Having described the invention, what is claimed is:
1. A method for producing 5-t-butylisophthalic acid comprising: oxidizing 5-t-butyl-m-xylene with an oxygen-containing gas in the liquid-phase in a solvent comprising an aliphatic monocarboxylic acid having 2 to 6 carbon atoms, at an elevated pressure and a temperature in the range of from about 150° C. to about 230° C. and in the presence of an oxidation catalyst comprising cobalt, manganese, and bromine components, to form a product mixture comprising crude 5-t-butylisophthalic acid, wherein the atom ratio of cobalt, calculated as elemental cobalt, in the cobalt component of the catalyst-to-5-t-butyl-m-xylene in the liquid-phase oxidation is in the range of from about 0.1 to about 20 mga per gram mole of 5-t-butyl-m-xylene, the atom ratio of manganese, calculated as elemental manganese, in the manganese component of the catalyst-to-cobalt, calculated as elemental cobalt, in the cobalt component of the catalyst is in the range of from about 0.5 to about 3 mga per mga of cobalt, and the atom ratio of bromine, calculated as elemental bromine, in the bromine component of the catalyst-to-total cobalt and manganese, calculated as elemental cobalt and elemental manganese, in the cobalt and manganese components of the catalyst is in the range of from about 0.2 to about 0:5 mga per mga of total cobalt and manganese.

2. The method of claim 1 wherein the crude 5-t-butylisophthalic acid produced in claim 1 is thereafter crystallized by cooling the product mixture to a temperature in the range of from about 20° C. to about 120° C.; the resulting crystallized crude 5-t-butylisophthalic acid is separated from the product mixture at a temperature in the range of from about 20° C. to about 120° C.; and the resulting separated crude 5-t-butylisophthalic acid is then recrystallized from a recrystallization solvent comprising at least one of acetic acid and water, at a temperature in the range of from about 160° C. to about 260° C. and at a weight ratio of recrystallization solvent-to-separated crude 5-t-butylisophthalic acid in range of from about 2:1 to about 7:1 to form purified 5-t-butylisophthalic acid.

3. The method of claim 1 wherein the oxidation step is performed at a temperature in the range of from about 175° C. to about 205° C.

4. The method of claim 1 wherein the solvent in the oxidation step is a mixture of acetic acid and water containing from 1 to 20 weight percent of water in the reactor as introduced into the oxidation reactor and based on the weight of the total solvent.

5. The method of claim 1 wherein the atom ratio of cobalt, calculated as elemental cobalt, in the cobalt component of the catalyst-to-5-t-butyl-m-xylene in the liquid-phase oxidation is in the range of from about 1 to about 10 mga per gram mole of 5-t-butyl-m-xylene, the atom ratio of manganese, calculated as elemental manganese, in the manganese component of the catalyst-to-cobalt, calculated as elemental cobalt, in the cobalt component of the catalyst is in the range of from about 1 to about 3 mga per mga of cobalt, and the atom ratio of bromine, calculated as elemental bromine, in the bromine, calculated as elemental bromine, in the bromine component of the catalyst-to-total cobalt and manganese, calculated as elemental cobalt and elemental manganese, in the cobalt and manganese components of the catalyst is in the range of from about 0.2 to about 0.5 mga per mga of total cobalt and manganese.

6. The method of claim 2 wherein the recrystallization solvent comprises at least 80 weight percent of acetic acid and the remainder thereof is water.

7. The method of claim 2 wherein the solution of dissolved crude 5-t-butylisophthalic acid is contacted with hydrogen in the presence of a hydrogenation catalyst during its recrystallization from the recrystallization solvent.

* * * * *